United States Patent
McCombs et al.

(10) Patent No.: US 7,764,985 B2
(45) Date of Patent: Jul. 27, 2010

(54) SURGICAL NAVIGATION SYSTEM COMPONENT FAULT INTERFACES AND RELATED PROCESSES

(75) Inventors: Daniel L. McCombs, Germantown, TN (US); Robert C. Thornberry, Tallahassee, FL (US); Jody Stallings, Palm Harbor, FL (US)

(73) Assignee: Smith & Nephew, Inc., Memphis, TN (US)

( * ) Notice: Subject to any disclaimer, the term of this patent is extended or adjusted under 35 U.S.C. 154(b) by 831 days.

(21) Appl. No.: 10/897,857

(22) Filed: Jul. 23, 2004

(65) Prior Publication Data

US 2005/0119639 A1 Jun. 2, 2005

Related U.S. Application Data

(63) Continuation-in-part of application No. 10/689,103, filed on Oct. 20, 2003, now abandoned.

(51) Int. Cl.
  *A61B 5/05* (2006.01)
(52) U.S. Cl. ............... 600/429; 600/407; 600/417; 606/1; 606/54; 606/96; 606/130; 434/211; 434/284
(58) Field of Classification Search .......... 600/414, 600/429, 407, 417; 606/1, 54, 96, 130; 434/211, 434/284
See application file for complete search history.

(56) References Cited

U.S. PATENT DOCUMENTS 100,602 A 3/1870 Coes (Continued)

FOREIGN PATENT DOCUMENTS

DE 042 25 112 C 12/1993

(Continued)

OTHER PUBLICATIONS

Smith & Nephew Total Hip Replacement Surgery, HipReplacementInfo.com, 3 pages, Nov. 8, 2005 http://www/hipreplacementinfo.com/hip-total-replacement.htm.

(Continued)

*Primary Examiner*—Brian Casler
*Assistant Examiner*—Joel M Lamprecht
(74) *Attorney, Agent, or Firm*—Kilpatrick Stockton LLP

(57) ABSTRACT

Devices and processes for use in computer aided or computer navigated surgery include one or more fault interfaces interposed between an indicium and an item to be used during surgery such as a body part, tool, implant, trial or other structure or component. After the indicia have been registered into the system and surgery begun, it is sometimes the case that indicia can be inadvertently moved or dislodged in position and/or orientation relative to the body part. Fault interfaces according to various embodiments are designed to fail first, so that the indicia can be repositioned relative to the item without the need to reregister the indicia into the system relative to the item. The fault interfaces preferably include structure that allows the indicium to be repositioned relative to the item so that it does not need to be reregistered into the system. Frame attachments which can by easily manufactured at relatively low cost, are disposable, and which are manufactured for single use are disclosed.

17 Claims, 8 Drawing Sheets

U.S. PATENT DOCUMENTS

| | | | | | |
|---|---|---|---|---|---|
| 1,076,971 | A | 10/1913 | Geiger |
| 1,201,467 | A | 10/1916 | Hoglund |
| 2,092,869 | A | 9/1937 | Baum |
| 3,412,733 | A | 11/1968 | Ross |
| 3,457,922 | A | 7/1969 | Ray |
| 3,702,611 | A | 11/1972 | Fishbein |
| 4,305,394 | A | 12/1981 | Bertuch, Jr. |
| 4,323,080 | A | 4/1982 | Melharty |
| 4,421,112 | A | 12/1983 | Mains et al. |
| 4,456,010 | A | 6/1984 | Relmels et al. |
| 4,457,307 | A | 7/1984 | Stillwell |
| 4,483,554 | A | 11/1984 | Ernst |
| 4,524,766 | A | 6/1985 | Petersen |
| 4,534,364 | A | 8/1985 | Lamoreux |
| 4,565,192 | A | 1/1986 | Shapiro |
| 4,566,448 | A | 1/1986 | Rohr, Jr. |
| 4,567,885 | A | 2/1986 | Androphy |
| 4,567,886 | A | 2/1986 | Petersen |
| 4,574,794 | A | 3/1986 | Cooke et al. |
| 4,583,554 | A | 4/1986 | Mittelman et al. |
| 4,671,275 | A | 6/1987 | Deyerle |
| 4,703,751 | A | 11/1987 | Pohl |
| 4,712,951 | A | 12/1987 | Brown |
| 4,718,413 | A | 1/1988 | Johnson |
| 4,722,056 | A | 1/1988 | Roberts et al. |
| 4,738,256 | A | 4/1988 | Freeman et al. |
| 4,759,350 | A | 7/1988 | Dunn et al. |
| 4,768,504 | A | 9/1988 | Ender |
| 4,777,942 | A | 10/1988 | Frey et al. |
| 4,802,468 | A | 2/1989 | Powlan |
| 4,803,976 | A | 2/1989 | Frigg et al. |
| 4,809,689 | A | 3/1989 | Anapliotis |
| 4,815,899 | A | 3/1989 | Regan |
| 4,875,475 | A | 10/1989 | Comte et al. |
| 4,892,093 | A | 1/1990 | Zarnowski et al. |
| 4,913,163 | A | 4/1990 | Roger et al. |
| 4,938,762 | A | 7/1990 | Wehrli |
| 4,952,213 | A | 8/1990 | Bowman et al. |
| 4,964,862 | A | 10/1990 | Arms |
| 4,991,579 | A | 2/1991 | Allen |
| 5,002,545 | A | 3/1991 | Whiteside et al. |
| 5,002,578 | A | 3/1991 | Luman |
| 5,016,639 | A | 5/1991 | Allen |
| 5,037,423 | A | 8/1991 | Kenna |
| 5,037,426 | A | 8/1991 | Goble et al. |
| 5,049,149 | A | 9/1991 | Schmidt |
| 5,053,039 | A | 10/1991 | Hofmann et al. |
| 5,078,719 | A | 1/1992 | Schreiber |
| 5,092,869 | A | 3/1992 | Waldron |
| 5,094,241 | A | 3/1992 | Allen |
| 5,097,839 | A | 3/1992 | Allen |
| 5,098,426 | A | 3/1992 | Sklar et al. |
| 5,116,338 | A | 5/1992 | Poggie et al. |
| 5,119,817 | A | 6/1992 | Allen |
| 5,122,144 | A | 6/1992 | Bert et al. |
| 5,129,909 | A | 7/1992 | Sutherland |
| 5,147,408 | A | 9/1992 | Noble |
| 5,190,547 | A | 3/1993 | Barber, Jr. et al. |
| 5,211,164 | A | 5/1993 | Allen |
| 5,213,312 | A | 5/1993 | MacDonald |
| 5,217,499 | A | 6/1993 | Shelley |
| 5,230,338 | A | 7/1993 | Allen et al. |
| 5,246,444 | A | 9/1993 | Schreiber |
| 5,254,119 | A | 10/1993 | Schreiber |
| 5,263,972 | A | 11/1993 | Evans et al. |
| 5,289,826 | A | 3/1994 | Kovacevic |
| 5,305,203 | A | 4/1994 | Raab |
| 5,342,366 | A | 8/1994 | Whiteside et al. |
| 5,360,016 | A | 11/1994 | Kovacevic |
| 5,364,401 | A | 11/1994 | Ferrante et al. |
| 5,364,402 | A | 11/1994 | Mumme et al. |
| 5,365,996 | A | 11/1994 | Crook |
| 5,375,588 | A | 12/1994 | Yoon |
| 5,379,133 | A | 1/1995 | Kirk |
| 5,383,454 | A | 1/1995 | Bucholz |
| 5,387,218 | A | 2/1995 | Meswania et al. |
| 5,389,101 | A | 2/1995 | Heilbrun et al. |
| 5,395,376 | A | 3/1995 | Caspari et al. |
| 5,397,329 | A | 3/1995 | Allen |
| 5,403,320 | A | 4/1995 | Luman |
| 5,423,828 | A | 6/1995 | Benson |
| 5,425,355 | A | 6/1995 | Kulick |
| 5,445,166 | A | 8/1995 | Taylor |
| 5,445,642 | A | 8/1995 | McNulty et al. |
| 5,449,360 | A | 9/1995 | Schreiber |
| 5,452,407 | A | 9/1995 | Crook |
| 5,462,548 | A | 10/1995 | Pappas et al. |
| 5,462,549 | A | 10/1995 | Glock |
| 5,468,244 | A | 11/1995 | Attfield et al. |
| 5,470,354 | A | 11/1995 | Hershberger et al. |
| 5,474,559 | A | 12/1995 | Bertin et al. |
| 5,484,437 | A | 1/1996 | Michelson |
| 5,486,178 | A | 1/1996 | Hodge |
| 5,490,854 | A | 2/1996 | Fisher et al. |
| 5,491,510 | A | 2/1996 | Gove |
| 5,507,824 | A | 4/1996 | Lennox |
| 5,514,139 | A | 5/1996 | Goldstein et al. |
| 5,517,990 | A | 5/1996 | Kalfas et al. |
| 5,534,366 | A | 7/1996 | Hwang et al. |
| 5,540,691 | A | 7/1996 | Elstrom et al. |
| 5,540,694 | A | 7/1996 | DeCarlo, Jr. |
| 5,540,695 | A | 7/1996 | Levy |
| 5,540,696 | A | 7/1996 | Booth, Jr. et al. |
| 5,569,260 | A | 10/1996 | Petersen |
| 5,597,379 | A | 1/1997 | Haines et al. |
| 5,598,269 | A | 1/1997 | Kitaevich et al. |
| 5,603,318 | A | 2/1997 | Heilbrun et al. |
| 5,613,969 | A | 3/1997 | Jenkins, Jr. |
| 5,643,268 | A | 7/1997 | Vilsmeier et al. |
| 5,643,272 | A | 7/1997 | Haines et al. |
| 5,658,290 | A | 8/1997 | Lechot |
| 5,669,914 | A | 9/1997 | Eckhoff |
| 5,676,668 | A | 10/1997 | McCue et al. |
| 5,681,316 | A | 10/1997 | DeOrio et al. |
| 5,682,886 | A | 11/1997 | Delp et al. |
| 5,683,397 | A | 11/1997 | Vendrely et al. |
| 5,688,279 | A | 11/1997 | McNulty et al. |
| 5,693,056 | A | 12/1997 | Carls et al. |
| 5,695,501 | A | 12/1997 | Carol et al. |
| 5,702,406 | A | 12/1997 | Vilsmeier et al. |
| 5,704,941 | A | 1/1998 | Jacober et al. |
| 5,707,370 | A | 1/1998 | Berki et al. |
| 5,709,689 | A | 1/1998 | Ferrante et al. |
| 5,715,836 | A | 2/1998 | Kliegis et al. |
| 5,716,361 | A | 2/1998 | Masini |
| 5,720,752 | A | 2/1998 | Elliott et al. |
| 5,722,978 | A | 3/1998 | Jenkins, Jr. |
| 5,733,292 | A | 3/1998 | Gustilo et al. |
| 5,735,904 | A | 4/1998 | Pappas |
| 5,743,915 | A | 4/1998 | Bertin et al. |
| 5,748,767 | A | 5/1998 | Raab |
| 5,755,725 | A | 5/1998 | Druais |
| 5,755,803 | A | 5/1998 | Haines et al. |
| 5,769,861 | A | 6/1998 | Vilsmeier |
| 5,772,593 | A | 6/1998 | Hakamata |
| 5,772,594 | A | 6/1998 | Barrick |
| 5,776,064 | A | 7/1998 | Kalfas et al. |
| 5,782,842 | A | 7/1998 | Kloess et al. |
| 5,792,147 | A | 8/1998 | Evans et al. |
| 5,797,924 | A | 8/1998 | Schulte et al. |
| 5,799,055 | A | 8/1998 | Peshkin et al. |
| 5,800,352 | A | 9/1998 | Ferre et al. |
| 5,800,438 | A | 9/1998 | Tuke et al. |
| 5,807,252 | A | 9/1998 | Hassfeld et al. |

| Patent Number | Date | Inventor(s) | Patent Number | Date | Inventor(s) |
|---|---|---|---|---|---|
| 5,810,827 A | 9/1998 | Haines et al. | 6,168,627 B1 | 1/2001 | Huebner |
| 5,810,841 A | 9/1998 | McNeirney et al. | 6,174,335 B1 | 1/2001 | Varieur |
| 5,817,097 A | 10/1998 | Howard et al. | 6,185,315 B1 | 2/2001 | Schmucker et al. |
| 5,830,214 A | 11/1998 | Flom et al. | 6,187,010 B1 | 2/2001 | Masini |
| 5,836,954 A | 11/1998 | Heilbrun et al. | 6,190,320 B1 | 2/2001 | Lelong |
| 5,848,967 A | 12/1998 | Cosman | 6,190,395 B1 | 2/2001 | Williams |
| 5,850,836 A | 12/1998 | Steiger et al. | 6,195,168 B1 | 2/2001 | De Lega et al. |
| 5,860,981 A | 1/1999 | Bertin et al. | 6,197,064 B1 | 3/2001 | Haines et al. |
| 5,865,809 A | 2/1999 | Moenning et al. | 6,198,794 B1 | 3/2001 | Peshkin et al. |
| 5,871,018 A | 2/1999 | Delp et al. | 6,200,316 B1 | 3/2001 | Zwirkoski et al. |
| 5,871,445 A | 2/1999 | Bucholz | 6,205,411 B1 | 3/2001 | DiGioia, III et al. |
| 5,879,352 A | 3/1999 | Filoso et al. | 6,211,976 B1 | 4/2001 | Popovich et al. |
| 5,879,354 A | 3/1999 | Haines et al. | 6,214,011 B1 | 4/2001 | Masini |
| 5,880,976 A | 3/1999 | DiGioia, III et al. | 6,216,029 B1 | 4/2001 | Paltieli |
| 5,885,296 A | 3/1999 | Masini | 6,223,067 B1 | 4/2001 | Vilsmeier et al. |
| 5,885,297 A | 3/1999 | Matsen, III | 6,226,548 B1 | 5/2001 | Foley et al. |
| 5,897,559 A | 4/1999 | Masinie | 6,228,090 B1 | 5/2001 | Waddell |
| 5,916,221 A | 6/1999 | Hodorek et al. | 6,228,092 B1 | 5/2001 | Mikhail |
| 5,920,395 A | 7/1999 | Schulz | 6,235,038 B1 | 5/2001 | Hunter et al. |
| 5,921,992 A | 7/1999 | Costales et al. | 6,236,875 B1 | 5/2001 | Bucholz et al. |
| 5,925,049 A | 7/1999 | Gustilo et al. | 6,241,735 B1 | 6/2001 | Marmulla |
| 5,935,128 A | 8/1999 | Carter et al. | 6,249,581 B1 | 6/2001 | Kok |
| 5,938,665 A | 8/1999 | Martin | 6,258,095 B1 | 7/2001 | Lombardo et al. |
| 5,944,722 A | 8/1999 | Masini | 6,258,096 B1 | 7/2001 | Seki |
| 5,947,971 A | 9/1999 | Kuslich et al. | 6,264,647 B1 | 7/2001 | Lechot |
| 5,947,973 A | 9/1999 | Masini | 6,283,971 B1 | 9/2001 | Temeles |
| 5,951,561 A | 9/1999 | Pepper et al. | 6,285,902 B1 | 9/2001 | Kienzle, III et al. |
| 5,957,926 A | 9/1999 | Masini | 6,295,513 B1 | 9/2001 | Thackston |
| 5,961,523 A | 10/1999 | Masini | 6,317,616 B1 | 11/2001 | Glossop |
| 5,971,989 A | 10/1999 | Masini | 6,319,256 B1 | 11/2001 | Spotorno |
| 5,980,526 A | 11/1999 | Johnson et al. | 6,332,891 B1 | 12/2001 | Himes |
| 5,980,535 A | 11/1999 | Barnett et al. | 6,333,971 B2 | 12/2001 | McCrory et al. |
| 5,999,837 A | 12/1999 | Messner et al. | 6,344,853 B1 | 2/2002 | Knight |
| 6,001,106 A | 12/1999 | Ryan et al. | 6,347,240 B1 | 2/2002 | Foley et al. |
| 6,002,859 A | 12/1999 | DiGioia, III et al. | 6,351,659 B1 | 2/2002 | Vilsmeier |
| 6,006,126 A | 12/1999 | Cosman | 6,351,661 B1 | 2/2002 | Cosman |
| 6,006,127 A | 12/1999 | Van Der Brug et al. | 6,377,839 B1 | 4/2002 | Kalfas et al. |
| 6,007,537 A | 12/1999 | Burkinshaw et al. | 6,381,485 B1 * | 4/2002 | Hunter et al. ................ 600/407 |
| 6,010,506 A | 1/2000 | Gosney et al. | 6,383,188 B2 | 5/2002 | Kuslich et al. |
| 6,011,987 A | 1/2000 | Barnett | 6,385,475 B1 | 5/2002 | Cinquin et al. |
| 6,016,606 A | 1/2000 | Oliver et al. | 6,405,072 B1 | 6/2002 | Cosman |
| 6,021,342 A | 2/2000 | Brabrand | 6,413,261 B1 | 7/2002 | Grundei |
| 6,021,343 A | 2/2000 | Foley et al. | 6,434,507 B1 | 8/2002 | Clayton et al. |
| 6,022,377 A | 2/2000 | Nuelle et al. | 6,440,140 B2 | 8/2002 | Bullivant et al. |
| 6,026,315 A | 2/2000 | Lenz et al. | 6,443,956 B1 | 9/2002 | Ray |
| 6,030,391 A | 2/2000 | Brainard et al. | 6,451,059 B1 | 9/2002 | Janas et al. |
| 6,033,410 A | 3/2000 | McLean et al. | 6,458,135 B1 | 10/2002 | Harwin et al. |
| 6,041,249 A | 3/2000 | Regn | 6,463,351 B1 | 10/2002 | Clynch |
| 6,044,291 A | 3/2000 | Rockseisen | 6,468,202 B1 | 10/2002 | Irion et al. |
| 6,045,556 A | 4/2000 | Cohen | 6,477,400 B1 | 11/2002 | Barrick |
| 6,050,724 A | 4/2000 | Schmitz et al. | 6,478,799 B1 | 11/2002 | Williamson |
| 6,053,922 A | 4/2000 | Krause et al. | 6,484,049 B1 | 11/2002 | Seeley et al. |
| 6,056,756 A | 5/2000 | Eng et al. | 6,490,467 B1 | 12/2002 | Bucholz et al. |
| 6,068,633 A | 5/2000 | Masini | 6,491,429 B1 | 12/2002 | Suhm |
| 6,069,932 A | 5/2000 | Peshkin et al. | 6,491,702 B2 | 12/2002 | Heilbrun et al. |
| 6,073,044 A | 6/2000 | Fitzpatrick et al. | 6,503,249 B1 | 1/2003 | Krause |
| 6,077,269 A | 6/2000 | Masini | 6,503,254 B2 | 1/2003 | Masini |
| 6,081,336 A | 6/2000 | Messner et al. | 6,527,443 B1 | 3/2003 | Vilsmeier et al. |
| 6,083,163 A | 7/2000 | Wegner et al. | 6,540,739 B2 | 4/2003 | Lechot |
| 6,096,048 A * | 8/2000 | Howard et al. ............... 606/130 | 6,546,279 B1 | 4/2003 | Bova et al. |
| 6,102,916 A | 8/2000 | Masini | 6,551,319 B2 | 4/2003 | Lieberman |
| 6,132,433 A | 10/2000 | Whelan | 6,551,324 B2 | 4/2003 | Muller |
| 6,143,390 A | 11/2000 | Takamiya et al. | 6,551,325 B2 | 4/2003 | Neubauer et al. |
| 6,144,875 A | 11/2000 | Schweikard et al. | 6,554,837 B1 | 4/2003 | Hauri et al. |
| 6,146,390 A | 11/2000 | Heilbrun et al. | 6,558,391 B2 | 5/2003 | Axelson, Jr. et al. |
| 6,148,280 A | 11/2000 | Kramer | 6,558,421 B1 | 5/2003 | Fell et al. |
| 6,161,033 A | 12/2000 | Kuhn | 6,567,687 B2 | 5/2003 | Front et al. |
| 6,162,190 A | 12/2000 | Kramer | 6,574,493 B2 | 6/2003 | Rasche et al. |
| 6,165,181 A | 12/2000 | Heilbrun et al. | 6,595,997 B2 | 7/2003 | Axelson, Jr. et al. |
| 6,167,145 A | 12/2000 | Foley et al. | 6,602,259 B1 | 8/2003 | Masini |
| 6,167,292 A | 12/2000 | Badano et al. | 6,620,168 B1 | 9/2003 | Lombardo et al. |
| 6,167,295 A | 12/2000 | Cosman | 6,620,268 B2 | 9/2003 | Cho et al. |
| 6,167,296 A | 12/2000 | Shahidi | 6,640,127 B1 | 10/2003 | Kosaka et al. |

| | | | | | |
|---|---|---|---|---|---|
| 6,652,142 B2 | 11/2003 | Launay et al. | 2002/0198448 A1 | 12/2002 | Zuk et al. |
| 6,662,036 B2 | 12/2003 | Cosman | 2002/0198451 A1 | 12/2002 | Carson |
| 6,673,077 B1 | 1/2004 | Katz | 2002/0198531 A1 | 12/2002 | Millard et al. |
| 6,675,040 B1 | 1/2004 | Cosman | 2003/0006107 A1 | 1/2003 | Thompson |
| 6,685,711 B2 | 2/2004 | Axelson, Jr. et al. | 2003/0018338 A1 | 1/2003 | Axelson, Jr. et al. |
| 6,690,964 B2 | 2/2004 | Bieger et al. | 2003/0030787 A1 | 2/2003 | Bradbury |
| 6,692,447 B1 | 2/2004 | Picard | 2003/0045883 A1 | 3/2003 | Chow et al. |
| 6,695,848 B2 | 2/2004 | Haines | 2003/0050643 A1 | 3/2003 | Taft |
| 6,702,821 B2 | 3/2004 | Bonutti | 2003/0069591 A1 | 4/2003 | Carson |
| 6,711,431 B2 | 3/2004 | Sarin et al. | 2003/0073901 A1 | 4/2003 | Simon et al. |
| 6,712,823 B2 | 3/2004 | Grusin et al. | 2003/0153829 A1 | 8/2003 | Sarin et al. |
| 6,712,824 B2 | 3/2004 | Millard et al. | 2003/0153859 A1 | 8/2003 | Hinshon |
| 6,716,249 B2 | 4/2004 | Hyde | 2003/0153978 A1 | 8/2003 | Whiteside |
| 6,718,194 B2 | 4/2004 | Kienzle | 2003/0164172 A1 | 9/2003 | Chumas et al. |
| 6,725,080 B2 | 4/2004 | Melkent et al. | 2003/0181918 A1 | 9/2003 | Smothers et al. |
| 6,725,082 B2 | 4/2004 | Sati et al. | 2003/0187351 A1 | 10/2003 | Franck et al. |
| 6,728,599 B2 | 4/2004 | Wang et al. | 2003/0187452 A1 | 10/2003 | Smith et al. |
| 6,772,026 B2 | 8/2004 | Bradbury et al. | 2003/0192557 A1 | 10/2003 | Krag et al. |
| 6,780,190 B2 | 8/2004 | Maroney | 2003/0225329 A1 | 12/2003 | Rossner et al. |
| 6,785,593 B2 | 8/2004 | Wang | 2004/0019382 A1 | 1/2004 | Amirouche et al. |
| 6,799,088 B2 | 9/2004 | Wang | 2004/0030237 A1 | 2/2004 | Lee et al. |
| 6,814,490 B1 | 11/2004 | Suhm et al. | 2004/0030245 A1 | 2/2004 | Noble et al. |
| 6,827,723 B2 | 12/2004 | Carson | 2004/0039396 A1 | 2/2004 | Couture et al. |
| 6,836,703 B2 | 12/2004 | Wang | 2004/0054489 A1 | 3/2004 | Moctezuma De La Barrera |
| 6,871,117 B2 | 3/2005 | Wang | 2004/0073279 A1 | 4/2004 | Malackowski et al. |
| 6,882,982 B2 | 4/2005 | McMenimen | 2004/0087852 A1 | 5/2004 | Chen et al. |
| 6,892,112 B2 | 5/2005 | Wang | 2004/0097952 A1 | 5/2004 | Sarin et al. |
| 6,905,514 B2 | 6/2005 | Carignan et al. | 2004/0152970 A1 | 8/2004 | Hunter et al. |
| 6,923,817 B2 | 8/2005 | Carson | 2004/0153081 A1 | 8/2004 | Tulkis |
| 6,947,786 B2 | 9/2005 | Simon et al. | 2004/0153083 A1 | 8/2004 | Nemec et al. |
| 6,993,374 B2 | 1/2006 | Sasso | 2004/0167391 A1 | 8/2004 | Solar et al. |
| 7,001,346 B2 | 2/2006 | White | 2004/0171924 A1 | 9/2004 | Mire et al. |
| 7,035,702 B2 | 4/2006 | Jelonek et al. | 2004/0243481 A1 | 12/2004 | Bradbury et al. |
| 7,237,556 B2 | 7/2007 | Smothers | 2004/0254586 A1 | 12/2004 | Sarin |
| 7,241,298 B2 | 7/2007 | Nemec et al. | 2004/0260290 A1 | 12/2004 | Zander et al. |
| 2001/0001120 A1 | 5/2001 | Masini | 2005/0021037 A1 | 1/2005 | McCombs et al. |
| 2001/0010004 A1 | 7/2001 | Traxel et al. | 2005/0021043 A1 | 1/2005 | Jansen |
| 2001/0014772 A1 | 8/2001 | Lampotang et al. | 2005/0049486 A1 * | 3/2005 | Urquhart et al. ............ 600/429 |
| 2001/0016745 A1 | 8/2001 | Bullivant et al. | 2005/0075632 A1 | 4/2005 | Russell et al. |
| 2001/0034530 A1 | 10/2001 | Malackowski et al. | 2005/0085715 A1 | 4/2005 | Dukesherer et al. |
| 2001/0036245 A1 | 11/2001 | Kienzle, III et al. | 2005/0085822 A1 | 4/2005 | Thornberry et al. |
| 2001/0039421 A1 | 11/2001 | Heilbrun et al. | 2005/0101966 A1 | 5/2005 | Lavailee |
| 2002/0002330 A1 | 1/2002 | Vilsmeier | 2005/0109855 A1 | 5/2005 | McCombs |
| 2002/0002365 A1 | 1/2002 | Lechot | 2005/0113658 A1 | 5/2005 | Jacobson et al. |
| 2002/0007294 A1 | 1/2002 | Bradbury et al. | 2005/0113659 A1 | 5/2005 | Pothier |
| 2002/0011594 A1 | 1/2002 | DeSouza | 2005/0113846 A1 | 5/2005 | Carson |
| 2002/0016540 A1 | 2/2002 | Mikus et al. | 2005/0119639 A1 | 6/2005 | McCombs |
| 2002/0018981 A1 | 2/2002 | Andersson et al. | 2005/0119777 A1 | 6/2005 | Arbogast et al. |
| 2002/0029041 A1 | 3/2002 | Hover et al. | 2005/0124988 A1 | 6/2005 | Terrill-Grisoni et al. |
| 2002/0032451 A1 | 3/2002 | Tierney et al. | 2005/0148843 A1 | 7/2005 | Roose |
| 2002/0038085 A1 | 3/2002 | Immerz | 2005/0149003 A1 | 7/2005 | Tierney et al. |
| 2002/0052606 A1 | 5/2002 | Bonutti | 2005/0149041 A1 | 7/2005 | McGinley |
| 2002/0065461 A1 | 5/2002 | Cosman | 2005/0154331 A1 | 7/2005 | Christie et al. |
| 2002/0068942 A1 | 6/2002 | Neubauer et al. | 2005/0159759 A1 | 7/2005 | Harbaugh et al. |
| 2002/0072748 A1 | 6/2002 | Robioneck | 2005/0177172 A1 | 8/2005 | Acker |
| 2002/0072821 A1 | 6/2002 | Baker | 2005/0197569 A1 | 9/2005 | McCombs |
| 2002/0077533 A1 | 6/2002 | Bieger et al. | 2005/0197814 A1 | 9/2005 | Aram et al. |
| 2002/0077540 A1 | 6/2002 | Kienzle, III | 2005/0203384 A1 | 9/2005 | Sati et al. |
| 2002/0085681 A1 | 7/2002 | Jensen | 2005/0209726 A1 | 9/2005 | Voit et al. |
| 2002/0087101 A1 | 7/2002 | Barrick et al. | 2005/0216305 A1 | 9/2005 | Funderud |
| 2002/0095081 A1 | 7/2002 | Vilsmeier | 2005/0228266 A1 | 10/2005 | McCombs |
| 2002/0102214 A1 * | 8/2002 | Briley-Saebo et al. ..... 424/9.36 | 2005/0228404 A1 | 10/2005 | Vandevelde |
| 2002/0107518 A1 | 8/2002 | Neubauer et al. | 2005/0234332 A1 | 10/2005 | Murphy |
| 2002/0115934 A1 | 8/2002 | Tuke | 2005/0234465 A1 | 10/2005 | McCombs |
| 2002/0133161 A1 | 9/2002 | Axelson et al. | 2005/0234466 A1 | 10/2005 | Stallings |
| 2002/0133175 A1 | 9/2002 | Carson | 2005/0234468 A1 | 10/2005 | Carson |
| 2002/0147455 A1 | 10/2002 | Carson | 2005/0245808 A1 | 11/2005 | Carson |
| 2002/0151894 A1 | 10/2002 | Melkent et al. | 2005/0279368 A1 | 12/2005 | McCombs |
| 2002/0151898 A1 | 10/2002 | Sohngen et al. | 2005/0288676 A1 | 12/2005 | Schnieders |
| 2002/0156371 A1 | 10/2002 | Hedlund et al. | 2006/0015120 A1 | 1/2006 | Richard et al. |
| 2002/0156479 A1 | 10/2002 | Schulzki et al. | 2006/0161051 A1 | 7/2006 | Terrill-Grisoni et al. |
| 2002/0188194 A1 | 12/2002 | Cosman | 2006/0190011 A1 | 8/2006 | Ries |
| 2002/0193800 A1 | 12/2002 | Kienzle, III et al. | 2006/0200025 A1 | 9/2006 | Elliott |

| | | |
|---|---|---|
| 2006/0229626 A1 | 10/2006 | McLean et al. |
| 2007/0118055 A1 | 5/2007 | McCombs |
| 2007/0123912 A1 | 5/2007 | Carson |
| 2007/0129629 A1 | 6/2007 | Beauregard et al. |
| 2007/0169782 A1 | 7/2007 | Smothers et al. |
| 2008/0269599 A1 | 10/2008 | Csavoy et al. |

FOREIGN PATENT DOCUMENTS

| | | |
|---|---|---|
| DE | 296 00 990 | 1/1996 |
| DE | 196 29 011 A1 | 1/1998 |
| DE | 197 09 960 A | 9/1998 |
| DE | 299 06 438 U1 | 9/1999 |
| DE | 296 23 941 U1 | 11/2000 |
| DE | 200 21 494 | 3/2001 |
| DE | 201 03 416 U1 | 7/2001 |
| DE | 100 12 042 | 8/2001 |
| DE | 100 31 887 A1 | 1/2002 |
| DE | 102 07 035 | 2/2002 |
| DE | 100 45 381 A1 | 4/2002 |
| DE | 202 13 243 | 10/2002 |
| DE | 203 09 399 | 8/2003 |
| EP | 0 327 509 A1 | 8/1989 |
| EP | 0 327 509 B1 | 8/1989 |
| EP | 0 337 901 A1 | 10/1989 |
| EP | 0 340 176 A2 | 11/1989 |
| EP | 0 216 794 B1 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 466 659 A2 | 1/1992 |
| EP | 0 359 097 | 8/1992 |
| EP | 0 538 152 A1 | 4/1993 |
| EP | 0 538 153 B1 | 4/1993 |
| EP | 0 555 003 B1 | 8/1993 |
| EP | 0 428 303 | 7/1995 |
| EP | 0 676 178 A | 10/1995 |
| EP | 0 720 834 A2 | 7/1996 |
| EP | 0 619 097 | 6/1999 |
| EP | 1 149 562 A2 | 10/2001 |
| EP | 1 033 108 | 2/2002 |
| EP | 1 190 676 B1 | 3/2002 |
| EP | 1 226 788 | 7/2002 |
| EP | 1 226 788 A1 | 7/2002 |
| EP | 0 782 842 | 9/2002 |
| EP | 1 236 450 A1 | 9/2002 |
| EP | 1 249 207 | 10/2002 |
| EP | 1 348 384 | 10/2003 |
| EP | 1 384 456 A2 | 1/2004 |
| EP | 1 405 603 A2 | 4/2004 |
| EP | 1 406 203 | 4/2004 |
| EP | 1 435 223 A1 | 7/2004 |
| EP | 1 442 715 | 8/2004 |
| EP | 1 459 686 A2 | 9/2004 |
| EP | 1 532 946 A2 | 5/2005 |
| EP | 1 563 795 | 8/2005 |
| FR | 2 828 397 | 2/2003 |
| GB | 2 224 937 | 5/1990 |
| GB | 2 397 769 A | 8/2004 |
| JP | 2002-304439 | 10/2002 |
| WO | WO 86/05384 | 9/1986 |
| WO | WO 89/09570 | 10/1989 |
| WO | WO 94/17733 | 8/1994 |
| WO | WO 95/15714 | 6/1995 |
| WO | WO 96/35387 | 11/1996 |
| WO | WO 97/16129 | 5/1997 |
| WO | WO 97/23172 | 7/1997 |
| WO | WO 97/29683 | 8/1997 |
| WO | WO 98/29032 | 7/1998 |
| WO | WO 98/46169 | 10/1998 |
| WO | WO 99/15097 | 4/1999 |
| WO | WO 99/27860 | 6/1999 |
| WO | WO 99/60939 | 12/1999 |
| WO | WO 99/65380 | 12/1999 |
| WO | WO 00/00093 | 1/2000 |
| WO | WO 00/21442 | 4/2000 |
| WO | WO 00/47103 | 8/2000 |
| WO | WO 00/64367 | 11/2000 |
| WO | WO 01/01845 A2 | 1/2001 |
| WO | WO 01/19271 A2 | 3/2001 |
| WO | WO 01/34050 A2 | 5/2001 |
| WO | WO 01/34050 A3 | 5/2001 |
| WO | WO 01/64124 A1 | 9/2001 |
| WO | WO 01/67979 A1 | 9/2001 |
| WO | WO 01/91647 A1 | 12/2001 |
| WO | WO 01/93770 A1 | 12/2001 |
| WO | WO 02/24096 A1 | 3/2002 |
| WO | WO 02/41794 A1 | 5/2002 |
| WO | WO 02/063236 A1 | 8/2002 |
| WO | WO 02/063236 A3 | 8/2002 |
| WO | WO 02/064042 | 8/2002 |
| WO | WO 02/067783 | 9/2002 |
| WO | WO 02/067784 | 9/2002 |
| WO | WO 02/067800 | 9/2002 |
| WO | WO 02/080824 A1 | 10/2002 |
| WO | WO 03/006107 | 1/2003 |
| WO | WO 03/015642 | 2/2003 |
| WO | WO 03/030787 | 4/2003 |
| WO | WO 03/034213 A2 | 4/2003 |
| WO | WO 03/034933 A1 | 5/2003 |
| WO | WO 03/037192 A1 | 5/2003 |
| WO | WO 03/039377 | 5/2003 |
| WO | WO 03/041566 A2 | 5/2003 |
| WO | WO 03/065931 | 8/2003 |
| WO | WO 03/065949 A2 | 8/2003 |
| WO | WO 03/068090 A1 | 8/2003 |
| WO | WO 03/071969 A1 | 9/2003 |
| WO | WO 03/075740 A2 | 9/2003 |
| WO | WO 03/079940 | 10/2003 |
| WO | WO 03/096870 A2 | 11/2003 |
| WO | WO 04/001569 A2 | 12/2003 |
| WO | WO 2004/017842 A2 | 3/2004 |
| WO | WO 2004/019792 | 3/2004 |
| WO | WO 2004/029908 A1 | 4/2004 |
| WO | WO 2004/030556 A2 | 4/2004 |
| WO | WO 2004/030559 A1 | 4/2004 |
| WO | WO 2004/046754 A2 | 6/2004 |
| WO | WO 2004/069036 | 8/2004 |
| WO | WO 2004/070580 | 8/2004 |
| WO | WO 2004/008740 A1 | 10/2004 |
| WO | WO 2004/084740 | 10/2004 |
| WO | WO 2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO2005/048851 A1 | 6/2005 |
| WO | WO2005/053559 A1 | 6/2005 |
| WO | WO 2005/057439 | 6/2005 |
| WO | WO2005/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2005/104977 | 11/2005 |
| WO | WO 2005/104978 | 11/2005 |
| WO | WO 2006/044367 A1 | 4/2006 |
| WO | WO 2006/060631 A1 | 6/2006 |
| WO | WO 2006/078236 A1 | 7/2006 |
| WO | WO 2008/021494 | 2/2008 |
| WO | WO 2008/064126 A2 | 5/2008 |

OTHER PUBLICATIONS

Smith & Nephew Brochure, Design Features, "Opera" pp. 4-15 (1999).

Corinth Surgeon Performs Revolutionary Hip Replacement, Mississippi Medical News, pp. 1-2 (Nov. 17, 2005) http://host1.bondware.com/~mississippi/news.php?viewStory=347.

Dario, et al., 'Smart Surgical Tools and Augmenting Devices,' IEEE Trans. Rob. Autom., 19(5):782-792 (2003).

Fernandez-Lozano, et al., 'Human-machine interface evaluation in a computer assisted surgical system,' Proc. IEEE Int. Conf. Rob. Autom., 2004:231-236 (2004).

Martelli, et al., 'Criteria of interface evaluation for computer assisted surgery systems,' Int. J. Med. Informatics, 72:35-45 (2003).

Visarius, et al., 'Man-machine interfaces in computer assisted surgery,' Computer Aided Surgery, pp. 102-107 (2004).

National Institute of Arthritis and Musculoskeletal and Skin Diseases (NIAMS), "Questions & Answers about . . . Knee Problems", 36 pp. (May 2001).

AO Development Institute "MEPUC Motorized Exact Positioning Unit for C-arm," one page (Jul. 7, 2003) http://www.ao-asif.ch/development/adi/examples/mepuc.shtml.

AO Development Institute "MEPUC Motorized Exact Positioning Unit . . . " one page (Mar. 26, 2003) http://www/ao-asif.ch/development/adi/examples/mepuc.shtml.

Barnes, et al., "Unicompartmental Knee Arthroplasty," *Bombay Hospital Journal*, Issue Special, pp. 1-5, www.bhj.org/journal/1996/3803_july/special_486.htm.

Bonecraft Carnegie Mellon Computer-Aided Bone Deformity Correction Brochure, pp. 1-5 (undated).

Bonutti, "Total Joint Replacement Surgery in the 21$^{st}$ Century—New 'Limited-Incision' Total Knee Replacement Offers Important Advantages," 01 page (undated).

Bonutti, et al., "Minimal Incision Total Knee Arthroplasty Using the Suspended Leg Technique," *Orthopedics*, (published Sep. 2003), 6 pages http://www.orthobluejournal.com/0903/9tips.asp.

BrainLAB Brochure entitled "Ortho . . . Your Partner for the Future" pp. 1-28 (2002).

Croitoru, et al., "Fixation-Based Surgery: A New Technique for Distal Radius Osteotomy," *Clinical Paper, Computer Aided Surgery* 2001, 160-169, vol. 6 (2001).

Delp, et al., "Computer-Assisted Knee Replacement," *Clinical Orthopaedics and Related Research*, 354:49-56 (1998).

Deluzio, et al., "Static alignment and the adduction moment in unicompartmental arthroplasty patients," Presented at NACOB 98: North American Congress on Biomechanics, University of Waterloo, Ontario, Canada, Aug. 14-18, 1998.

DiGioia, et al., "Computer Assisted Orthopedic Surgery," *Clinical Orthopaedics and Related Research*, Sep. 1998, vol. 354, pp. 8-16.

Ellis, et al., "A Surgical Planning and Guidance System for High Tibial Osteotomy," *Journal of Computer-Assisted Surgery*, 4(5):264-274 (1999).

Foley, et al., "Percutaneous pedicle screw fixation of the lumbar spine," *Neurosurg. Focus*, vol. 10(4), pp. 1-8 (2001).

Glossop, http:/www/traxta.com/papers/cua/mode1.html, 8 pages (Feb. 6, 2002).

iON™ Smith & Nephew Orthopaedics Brochure entitled "You'll Never Look At Your Patients The Same Way Again." 10 pages (Jan. 2001).

Iyun, et al., "Planning and Performing the Ilizarov Method with the Taylor Spatial Frame," Abstract, at 2$^{nd}$ Annual Meeting of International Society for Computer Assisted Orthopaedic Surgery, Jun. 21, 2002, pp. 145-147.

Kanade, et al., "Image-Based Computer Assisted Orthopedic Surgery System," Bonecraft, Inc., 12 pages, Apr. 30, 2001.

Kiefer, et al., "Computer Aided Knee Arthroplasty Versus Conventional Technique—First Results," First Annual Meeting of the International Society for Computer Assisted Orthopedic Surgery, Davos, Switzerland, Feb. 8-10, 2001.

Kunz, et al., "Development and Verification of a Non-CT Based Total Knee Arthroplasty System for the LCS Prosthesis," First Annual Meeting of the International Society for Computer Assisted Orthopedic Surgery, Davos, Switzerland, Feb. 8-10, 2001.

Medtronic Surgical Navigation Technologies "Overview Image-Guided Surgery An Advanced Solution to Traditional Surgery," two pages (undated).

Medtronic Surgical Navigation Technologies SNT VERTEK photograph, one page (undated).

Medtronic Surgical Navigation Technologies System Components photograph VERTEK Platform, one page (undated).

Munoz, et al., "Computer Assisted Planning of Hig Tibial Osteotomy for the Treatment of Knee Osteoarthritis," http://www.utc.fr/esb/esb09/abs_htm/570.html (Feb. 21, 2002) (three pages).

Patent Abstracts of Japan, vol. 2002, No. 05, May 3, 2002 & JP 2002 017740A (Ochi Takahiro; Yonenobu Sakuo: MMT:KK) Jan. 22, 2002 Abstract.

Picard, et al., "Kneenav.TKR: Concept and Clinical Application," Computer Assisted Orthopedic Surgery USA 2000 Meeting, Pittsburgh, PA., Jun. 15-17, 2000.

Saragaglia, et al., "Computer Assisted Total Knee Arthroplasty: Comparison with a Conventional Procedure. Results of a 50 Cases Prospective Randomized Study," First Annual Meeting of the International Society for Computer Assisted Orthopedic Surgery, Davos, Switzerland, Feb. 8-10, 2001.

Simon, et al., "The Fundamentals of Virtual Fluoroscopy," Medtronic Surgical Navigation Technologies, Medtronic, pp. 57-66, Computer Assisted Orthopedic Surgery USA 2000 Meeting, Pittsburgh, PA, Jun. 15-17, 2000.

Smith & Nephew—Orthopaedics—CAS—Knees Computer Assisted Total Knee Replacement Surgery, 02 pages (Oct. 13, 2004) http://ortho.smith-nephew.com/us/Standard.asp?NodeId=3396.

Smith & Nephew—Orthopaedics—TriGen Flexible Reamer System http://www.smithnephew.com/US/Standard.asp?NodeID=2998, 02 pages (Jan. 21, 2003).

Smith & Nephew—Orthopaedics—TriGen Reducer http://www.smithnephew.com/US/Standard.asp?NodeID=2996, one page (Jan. 21, 2003).

Smith & Nephew Brochure entitled "Surgical Technique Mini Incision Hip Posterior Approach," 20 pages (Mar. 2003).

Smith & Nephew First Choice in Orthopaedics Brochure Entitled "Achieve Computer Assisted Surgery Trauma Applications The Orbiter Base Station & Satellite Surgical Platform," 18 pages (undated).

Smith & Nephew Genesis II "Total Knee System Primary Surgical Technique," Brochure, pp. 1-36 (Mar. 2001).

Smith & Nephew Orthopaedic product bulletin, 01 page.

Smith & Nephew Richards Genesis® "Total Knee System Primary Surgical Technique Anterior Referencing Instrumentation," pp. 59 (Dec. 1993).

Smith & Nephew Richards Genesis® Total Knee System, "Revision Posterior Referencing Instrumentaion Surgical Technique," Brochure, pp. 1-51 (Dec. 1993).

Stryker Navigation System brochure entitled ". . . best alignment for gap kinematics," 6 pages (2001).

Sugano, et al., "Medical Robotics and Computer-Assisted Surgery in the Surgical Treatment of Patients and Rheumatic Diseases," *Cutting Edge Reports*, http://www/rheuma21st.com/archives/cutting_edge_Robotics_Japan.html (Apr. 27, 2000).

Suhm, et al., "Adapting the C-Arm Fluoroscope for Image Guided Orthopaedic Surgery," *CAOS*, pp. 212-214 (2002).

Tenbusch, et al., "First Results Using the Robodoc® System for Total Knee Replacement," First Annual Meeting of the International Society for Computer Assisted Orthopedic Surgrey, Davos, Switzerland, Feb. 8-10, 2001.

TRICON Total Knee System, "TRICON-M® with PRO-FIT™ Surgical Procedures," Richards Brochure, pp. 1-29 (undated).

Valstar, et al., "Towards computer-assisted surgery in should joint replacement," *ISPRS Journal of Photogrammetry & Remote Sensing*,56:326-337 (2002).

DePuy, a Johnson & Johnson Company, Brochure entitled 'S-ROM Modular Hip System Minimally Invasive Calcar Miller Surgical Technique,' 12 pages (2004).

Hafez, et al., 'Computer-assisted Total Knee Arthroplasty Using Patient-specific Templating,' *Clinical Orthopaedics and Related Research*, No. 444, pp. 184-192 (2006).

English-language abstract of CN 101224104 published on Jul. 23, 2008, Quan, Renfu, et al., Inventors.

* cited by examiner

SURGICAL NAVIGATION SYSTEM COMPONENT FAULT INTERFACES AND RELATED PROCESSES

CROSS REFERENCE TO RELATED APPLICATION

This application is a continuation-in-part application of, and claims priority to U.S. patent application Ser. No. 10/689,103 filed on Oct. 20, 2003 now abandoned.

FIELD OF THE INVENTION

The present invention relates to frame attachments for use in surgical navigation, and methods for their use. More specifically, the invention relates to frame attachments comprising fiducials or other reference structures which are designed to be accurately reinstalled into correct position if inadvertently or otherwise moved or altered with respect to their original registration in a surgical navigation system. The invention further relates to frame attachments which are disposable.

BACKGROUND

A major concern during surgical procedures as well as other medical operations is carrying out the procedures with as much precision as possible. For example, in orthopedic procedures, less than optimum alignment of implanted prosthetic components may cause undesired wear and revision, which may eventually lead to the failure of the implanted prosthesis. Other general surgical procedures also require precision in their execution.

With orthopedic procedures, for example, previous practices have not allowed for precise alignment of prosthetic components. For example, in a total knee arthroplasty, previous instrument design for resection of bone limited the alignment of the femoral and tibial resections to average value for varus/valgus, flexion/extension and external/internal rotation. Additionally, surgeons often use visual landmarks or "rules of thumb" for alignment which can be misleading due to anatomical variability. Intramedullary referencing instruments also violate the femoral and tibial canal. This intrusion increases the risk of fat embolism and unnecessary blood loss in the patient.

Devices and processes according to various embodiments of the present invention are applicable not only for knee repair, reconstruction or replacement surgery, but also repair, reconstruction or replacement surgery in connection with any other joint of the body as well as any other surgical or other operation where it is useful to track position and orientation of body parts, non-body components and/or virtual references such as rotational axes, and to display and output data regarding positioning and orientation of them relative to each other for use in navigation and performance of the operation.

Several manufacturers currently produce image-guided surgical navigation systems that are used to assist in performing surgical procedures with greater precision. The TREON™ and iON™ systems with FLUORONAV™ software manufactured by Medtronic Surgical Navigation Technologies, Inc. are examples of such systems. The BrainLAB VECTORVISION™ system is another example of such a surgical navigation system. Systems and methods for accomplishing image-guided surgery are also disclosed in U.S. Ser. No. 10/364,859, filed Feb. 11, 2003 and entitled "Image Guided Fracture Reduction," which claims priority to U.S. Ser. No. 60/355,886, filed Feb. 11, 2002 and entitled "Image Guided Fracture Reduction"; U.S. Ser. No. 60/271,818, filed Feb. 27, 2001 and entitled "Image Guided System for Arthroplasty"; U.S. Ser. No. 10/229,372, filed Aug. 27, 2002 and entitled "Computer Assisted Knee Arthroplasty Instrumentation, Systems and Processes"; U.S. Ser. No. 10/084,012 filed Feb. 27, 2002 and entitled "Total Knee Arthroplasty Systems and Processes," which claims priority to provisional application entitled "Surgical Navigation Systems and Processes," Ser. No. 60/355,899, filed Feb. 11, 2002; U.S. Ser. No. 10/084,278 filed Feb. 27, 2002 and entitled "Surgical Navigation Systems and Processes for Unicompartmental Knee Arthroplasty," which claims priority to provisional application entitled "Surgical Navigation Systems and Processes," Ser. No. 60/355,899, filed Feb. 11, 2002; U.S. Ser. No. 10/084,291 entitled "Surgical Navigation Systems and Processes for High Tibial Osteotomy," which claims priority to provisional application entitled "Surgical Navigation Systems and Processes," Ser. No. 60/355,899, filed Feb. 11, 2002; provisional application entitled "Image-guided Navigated Precisions Reamers," Ser. No. 60/474,178, filed May 29, 2003.

These systems and processes use position and/or orientation tracking sensors such as infrared sensors acting stereoscopically or other sensors acting in conjunction with reference structures or reference transmitters to track positions of body parts, surgery-related items such as implements, instrumentation, trial prosthetics, prosthetic components, and virtual constructs or references such as rotational axes which have been calculated and stored based on designation of bone landmarks. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated reference structures such as fiducials, reference transmitters, or based on stored position and/or orientation information. The processing functionality correlates this position and orientation information for each object with stored information, such as a computerized fluoroscopic imaged file, a wire frame data file for rendering a representation of an instrument component, trial prosthesis or actual prosthesis, or a computer generated file relating to a rotational axis or other virtual construct or reference. The processing functionality then displays position and orientation of these objects on a screen or monitor, or otherwise. Thus, systems or processes, by sensing the position of reference structures or transmitters, can display or otherwise output useful data relating to predicted or actual position and orientation of body parts, surgically related items, implants, and virtual constructs for use in navigation, assessment, and otherwise performing surgery or other operations.

Some of these reference structures or reference transmitters may emit or reflect infrared light that is then detected by an infrared camera. The references may be sensed actively or passively by infrared, visual, sound, magnetic, electromagnetic, x-ray or any other desired technique. An active reference emits energy, and a passive reference merely reflects energy. Reference structures may have at least three, but usually four, markers or fiducials that are traced by an infrared sensor to determine the position and orientation of the reference and thus the position and orientation of the associated instrument, implant component or other object to which the reference is attached.

In addition to reference structures with fixed fiducials, modular fiducials, which may be positioned independent of each other, may be used to reference points in the coordinate system. Modular fiducials may include reflective elements which may be tracked by two, sometimes more sensors whose output may be processed in concert by associated processing functionality to geometrically calculate the position and orientation of the item to which the modular fiducial is attached. Like fixed fiducial reference structures, modular fiducials and the sensors need not be confined to the infrared spectrum—any electromagnetic, electrostatic, light, sound, radio frequently or other desired technique may be used. Similarly, modular fiducials may "actively" transmit reference information to a tracking system, as opposed to "passively" reflecting infrared or other forms of energy.

Some image-guided surgical navigation systems allow reference structures to be detected at the same time the fluoroscopy imaging is occurring. This allows the position and orientation of the reference structure to be coordinated with the fluoroscope imaging. Then, after processing position and orientation data, the reference structures may be used to track the position and orientation of anatomical features that were recorded fluoroscopically. Computer-generated images of instruments, components, or other structures that are fitted with reference structures may be superimposed on the fluoroscopic images. The instruments, trial, implant or other structure or geometry can be displayed as 3-D models, outline models, or bone-implant interface surfaces.

Some image-guided surgical navigation systems monitor the location and orientation of the reference structures and consequently the portion of the anatomy or instruments secured to the reference structure by either actively or passively detecting the position of fiducials associated with the reference structure. Because the fiducials may be arranged in particular patterns, the system can determine the exact orientation and location of the reference structure associated with the fiducials. In other words, depending upon the particular location of the individual fiducials, the system will "see" the reference structure in a particular way and will be able to calculate the location and orientation of the reference structure based upon that data. Consequently, the system can determine the exact orientation and location of the portion of the anatomy or instrument associated with the reference structure.

The exact spatial relationship of the individual fiducials with respect to each other and the associated anatomy or instrument forms the basis of how a fiducial-based system calculates the position and orientation of the associated items. Similarly, the exact spatial relationship of a reference transmitter with respect to its associated anatomy or instrument forms the basis of how a transmitter-based system calculates the position and orientation of the associated anatomy or instruments. Consequently, once the spatial relationship of the fiducials or reference transmitter with respect to the associated item to be tracked has been registered in the system, subsequent changes in the position and/or orientation of the fiducials or reference transmitter may cause the system to erroneously calculate the position and orientation of the anatomy or instruments associated with the fiducials or reference transmitter. Even minor changes in orientation and/or position of the references may lead to dramatic differences in how the system detects the orientation and/or location of the associated anatomy or instruments. Such changes may require the system to be recalibrated, requiring additional fluoroscopy or other imaging to be obtained, increasing the time and the expense of the procedure. Failure to recalibrate the system may lead to imprecision in the execution of the desired surgical procedure.

In a busy operating room, there is a possibility that reference structures, or one or more fiducials on a reference structure, will be inadvertently deformed or displaced in position or orientation, such as by a surgeon or nurse's arm or elbow, after calibration. When this happens, the reference structures and/or fiducials will provide inaccurate information about the location, position, and orientation of the body parts, non-body components and other reference points previously placed in the coordinate system and the accuracy and safety of the surgical procedure may be jeopardized. Even where a surgeon or other surgery attendant tries to place the reference structure back in its original position, it is virtually impossible to relocate the original location, position and orientation with precision. And as discussed above, even the slightest change can have dramatic results.

As a result, when a reference structure or fiducial loses its original position in the reference system, the entire coordinate system must be recalibrated or reregistered. To continue with the image guided surgery, the surgeon must reregister each instrument that will be used in the procedure and each reference structure and fiducial that is on the patient or otherwise in the coordinate system. This process lengthens the time necessary to complete the surgical procedure and can result in unnecessary complications resulting from the additional length of time the patient is in surgery.

Adding to this concern is the tendency of some surgeons to not take the time necessary to recalibrate the entire system when a reference structure or fiducial is dislocated as described above. When this occurs, the virtual image created by the imaging system is not a true reflection of the actual position, orientation and relationship of the body parts, non-body components and other reference points. Proceeding with surgical procedures with a coordinate system under these conditions can lead to obvious dangers.

SUMMARY

Various aspects and embodiments of the present invention include frame attachments with portions that, when displaced or dislodged, will readily disconnect from a base secured to the reference point in the coordinate system and be able to be precisely repositioned.

According to one aspect of the present invention, a frame attachment includes a connecting portion with an interface designed to complement the receiving portion of a base secured in the coordinate system. The attachment device creates a stable connection with the base but, when displaced or dislodged, separates from the base without resulting in a change of location of the base within the coordinate system. The attachment can therefore be replaced without having to recalibrate the entire system.

According to another aspect, a frame attachment includes a connecting portion with an interface which is designed to complement a receiving portion of a base. The attachment device creates a stable connection with the base through the use of an additional connection aid, such as magnetic attraction, adhesive, hook and pile connectors, or any other material or force which creates a bond between the attachment device and base. The failure strength of the bond is preferably smaller than the failure strength of any portion of the attachment or the base. When the attachment device is displaced or dislodged, it separates from the base without resulting in a change of location of the base within the coordinate system. As such, the attachment device can be replaced without having to recalibrate the entire system.

According to other aspects of the present invention, the attachment device comprises fiducials, reference transmitters and/or other reference devices.

According to other aspects of the present invention, the base comprises a bone screw and/or other devices connected to a human body.

According to other aspects of the present invention, attachment devices and modular fiducials exhibit modularity such that they may be moved within a coordinate system without the disruption of the base secured within the coordinate system.

According to other aspects of the present invention, the fiducials are adapted for single use and are, thus, disposable. According to certain aspects of this embodiment, the fiducials are comprised of plastic.

DETAILED DESCRIPTION OF THE INVENTION

Figure 1:
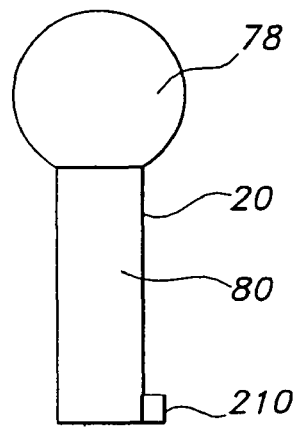
FIG. 1 shows a schematic side view of a modular fiducial according to one embodiment of the present invention.
Figure 3:
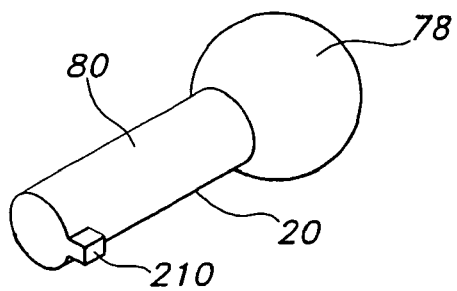
FIG. 3 shows a perspective view of the modular fiducial of FIG. 1.

FIGS. 1-5 illustrate one form of device according to one embodiment of the present invention. FIGS. 1 and 3 show a modular indicium 20 that includes a fiducial or reflective element 78, a stem 80, and a key 210. The indicium 20 can instead be a transponder using any energy within the energy spectrum as desired, or any other active or passive device which is able to impart position information to another device so that, when that device senses position of three or more indicia 20 rigidly attached to a body part, tool, implant, trial or other thing in the operating room, the device is able to generate position and orientation information about the thing. The indicium can be of any desired shape, size, structure, material, circuitry such as RFID, or any other physical instantiation. The device which senses the indicium 20 can be any of the conventional or unconventional computer aided surgery systems mentioned above or otherwise, which include an imager for sensing the position and location of the indicium 20, computer functionality for generating position and orientation information about the thing to which the indicium is attached, and a display device which can render the thing correctly located and oriented according to position of the indicia 20.

In the embodiment shown in these figures, the key 210 protrudes from the lower portion of the stem 80. Any structure can be used to create a fault interface that has a failure strength less than the failure strength of the indicium to reference frame connection, or the reference frame to body part or other thing connection, or the failure strength of any part of these components or relevant parts of them. Preferably, the fault interface permits the indicium to be repositioned with respect to the thing or item in only one position and orientation if inadvertently or otherwise dislodged. That position is the position in which the indicium was originally registered into the computer aided surgery system. The present invention includes, however, any fault interface that permits the indicium to be repositioned without the need to reregister the indicium in the system.

Figure 4:
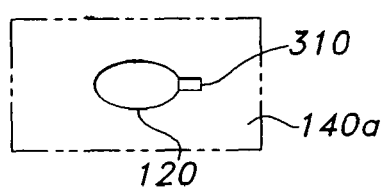
FIG. 4 shows a perspective view of the portion of the base having the fault interface of FIG. 2.
Figure 2:
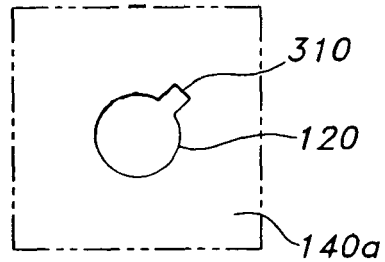
FIG. 2 shows a schematic top view of the portion of a base having the fault interface for connection with the modular fiducial of FIG. 1.
Figure 5:
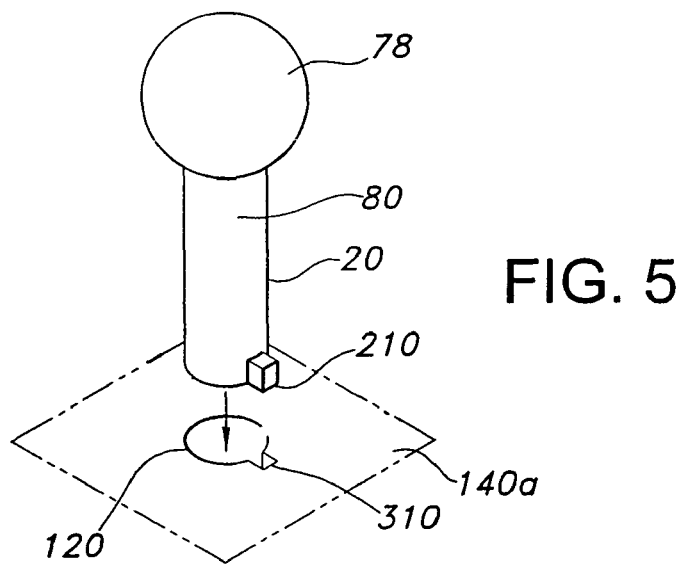
FIG. 5 shows a schematic view of the modular fiducial of FIG. 1 positioned for placement within the portion of the base having the fault interface of FIG. 2.

FIGS. 2 and 4 show a base 140a with a fault interface 120 for the modular fiducial 20. The base may include, without limitation, a pin, a plate, a platform, or any other device which is secured within a reference system. The fault interface 120 has a groove 310 for placement of the key 210. This key/groove arrangement requires that the fiducial 20 be positioned in only one orientation in order to fit correctly. As a result, when the fiducial is dislodged or displaced relative to the base, either by purpose or accident, it may be replaced within the base in the precise location, position and orientation as its original placement in the coordinate system thus removing the necessity for the recalibration of the entire reference system. Placement of the fiducial 20 onto the base 140a is depicted in FIG. 5.

While FIGS. 1-5 depict one embodiment of the present invention, the invention includes any interface that allows registration of indicium or an attachment device with a base which allows the indicium or attachment device to be repositioned without the need to reregister the indicium in the system. For instance, FIGS. 6-8 depict other structures according to other embodiments of the present invention.

Figure 6:
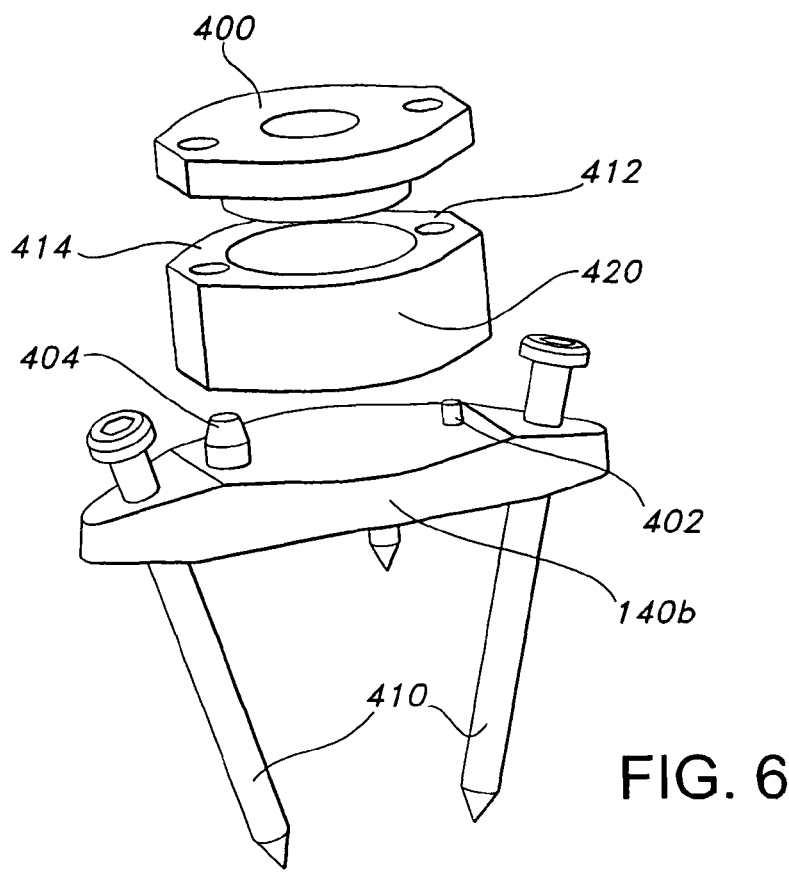
FIG. 6 shows a perspective view of an attachment device positioned for placement on top of a base according to another embodiment of the invention.

FIG. 6 shows an embodiment of the present invention in which the base 140b is in the form of a plate. The plate is securely attached to a body part or other reference point through the use of pins 410. In this embodiment, the base 140b includes two protrusions 402, 404 at the fault interface—a first protrusion 402 and a second protrusion 404. The protrusions are preferably of different size and/or shape, in order to allow another component to be attached in only one orientation. An attachment device 420 is included in this particular structure, which is designed to accept an additional element 400 for placement of a reference frame, fiducial or fiducials or other reference device or devices whether active or passive. The reference structure 420 includes two apertures 412, 414 which correspond in size and shape to protrusions 402, 404, whether or not those protrusions are of different size and/or shape. The design and placement of the protrusions and apertures preferably mandates that the attachment device 420 connects with the base 140b in only one position and orientation. Preferably, there is a friction fit at the fault interface which has a failure strength less than the failure strength of any part of, or relevant parts of any of components 140b, 400, or 420, and also less than the deformation limit or failure strength of the connection between the base 140b and the patient. Accordingly, when a fiducial, reference frame or other structure attached or connected, directly or indirectly to component 400 or 420 is dislodged or displaced, the attachment device 420 dislocates at the fault interface, but the base 140b remains securely in place. Because the design of the attachment device 420 and the base 140 allow connection in only position and orientation, however, the attachment device 420 may be precisely replaced on the base 140b and no further calibration is necessary before proceeding with surgery.

Figure 7:
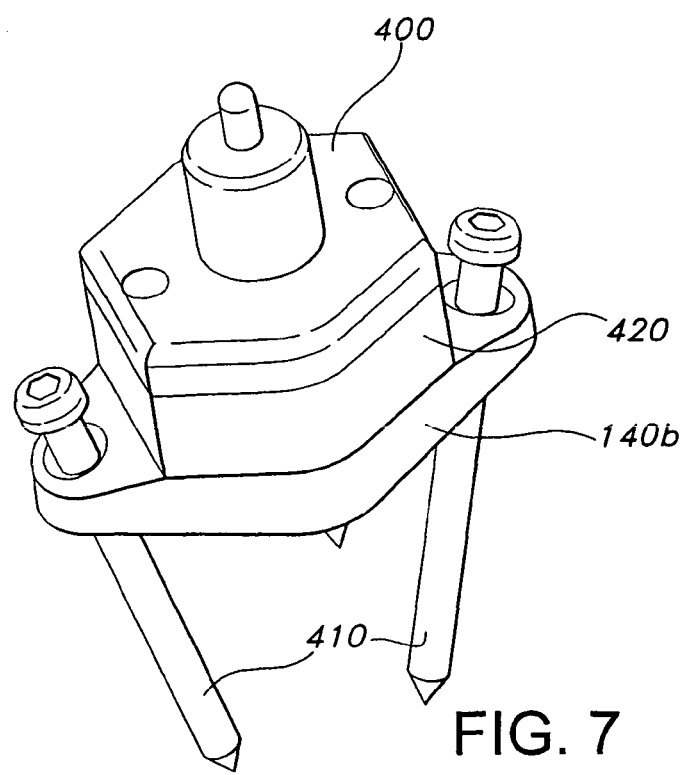
FIG. 7 shows a perspective view of an attachment device connected to a base according to another embodiment of the invention.

FIG. 7 shows a variation of the embodiment of FIG. 6 in which the attachment device 420 has been placed upon the base 140b. This embodiment includes an element 400 which can feature an active position indicating device or fiducial projecting above the surface of the element 400.

Figure 8:
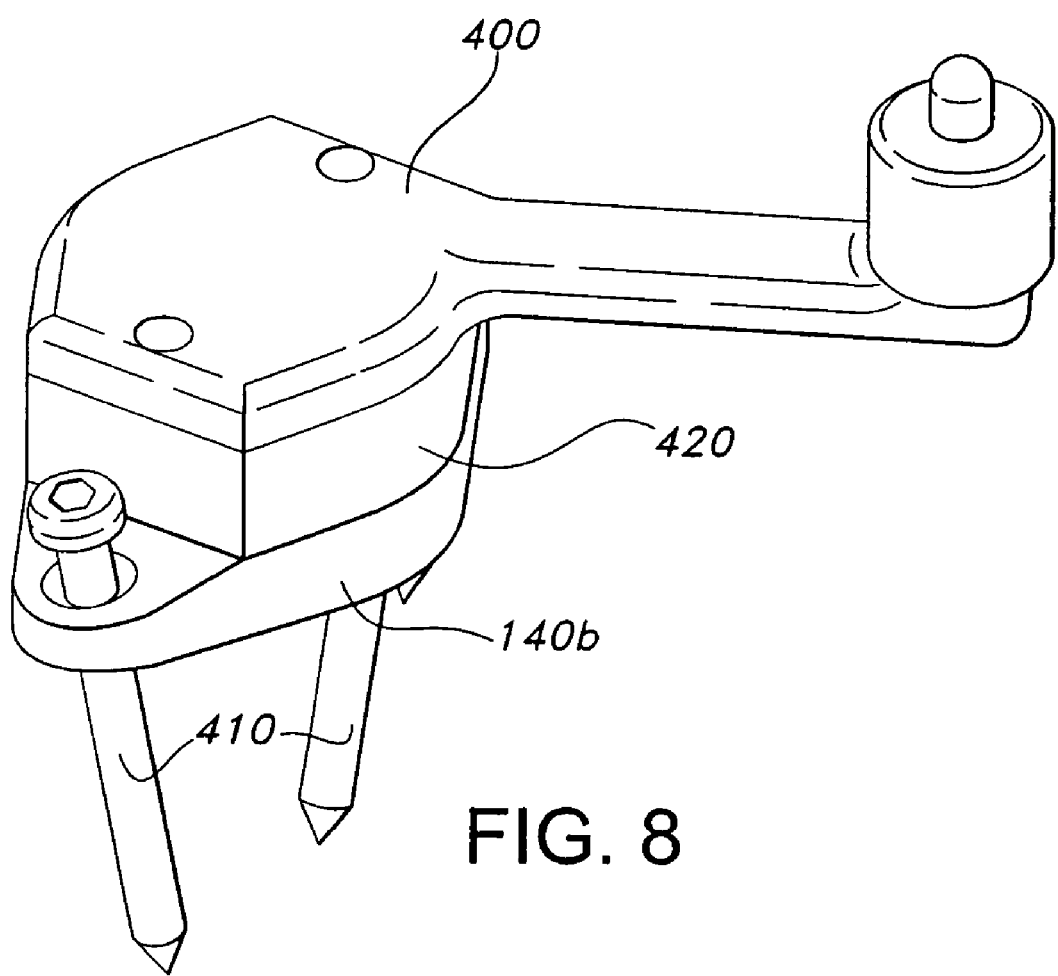
FIG. 8 shows a perspective view of an attachment device connected to a base according to still another embodiment of the present invention.

FIG. 8 shows yet another embodiment of the present invention. In this embodiment, the fiducial-accepting element 400 places the indicating device or fiducial outside the perimeter of the attachment device 420. However, the design of the attachment device 420 and the base 140b are such that, when sufficient force is exerted, the attachment device 420 dislodges while the base 140b remains securely in place allowing the attachment device 420 to be replaced in the same position and orientation. Therefore, the recalibration of the coordinate system is not necessary.

Figure 9:
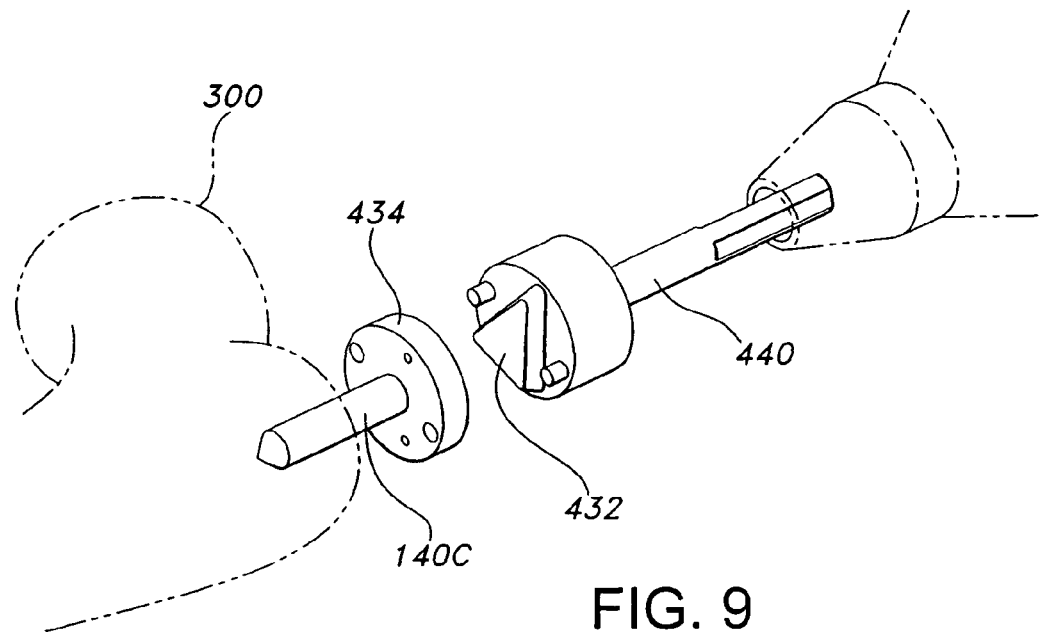
FIG. 9 shows a perspective view of a drill attachment according to another embodiment of the present invention positioned for connection to a bone screw.
Figure 10:
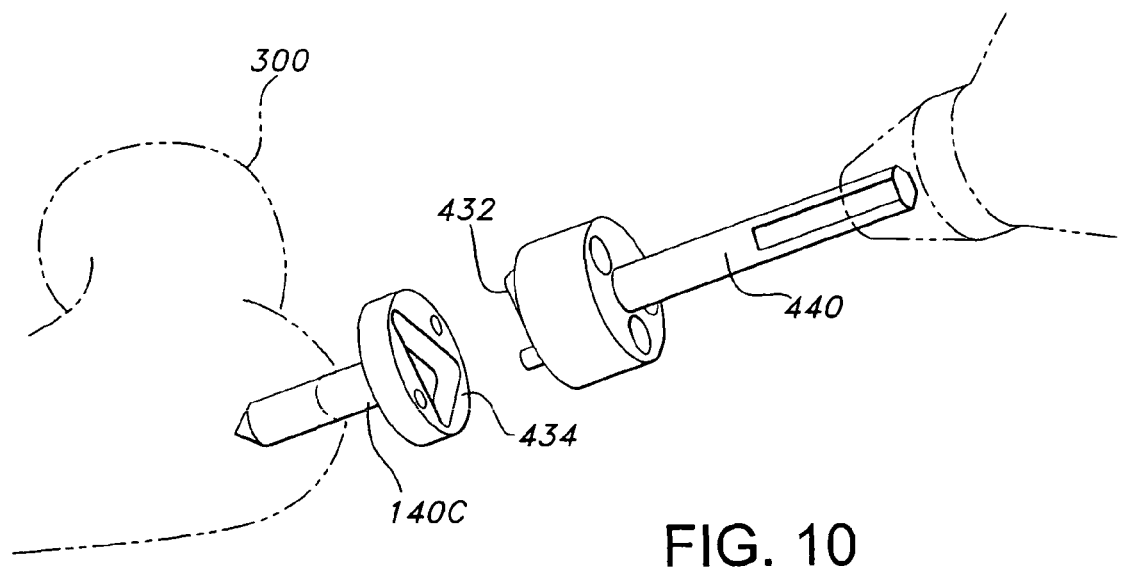
FIG. 10 shows another perspective view of a drill attachment device of FIG. 9 positioned for placement in a bone screw.

FIGS. 9 and 10 show another embodiment of the present invention in which the base 140c is in the form of a bone screw. The bone screw contains a fault interface 434 which corresponds to a pattern 432 on a drill attachment 440. This pattern is also present on the portion of the fiducial or other reference structure which attaches to the bone screw 140c. The interface on the bone screw 434 and corresponding pattern 432 require that the drill attachment 440 be positioned in only on orientation in order to fit correctly. The drill attachment 440 is connected to the bone screw 140c and the drill is used to secure the bone screw 140c to the bone 300.

Figure 11:
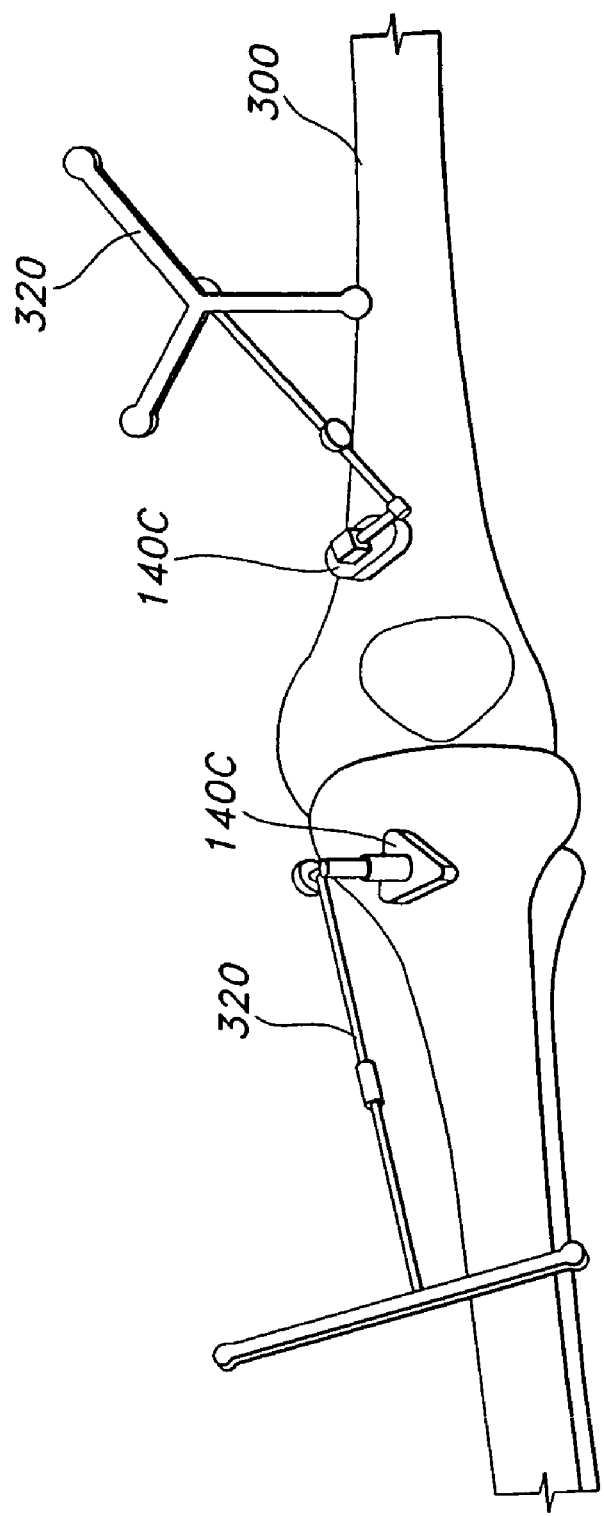
FIG. 11 shows a perspective view of an attachment device according to another aspect of the present invention connected to a bone screw.

FIG. 11 shows a variation of the embodiment of FIGS. 9 and 10 in which attachment devices 320 have been placed on the bone screws 140c which are connected to a bone 300. The design of the attachment device 320 and the base 140c are such that, when sufficient force is exerted, the attachment device 320 dislodges while the bone screw 140c remains securely in place allowing the attachment device 320 to be replaced in the same position and orientation. Therefore, the recalibration of the coordinate system is not necessary.

According to certain embodiments of the present invention, a connection aid provides further support for the connection between the fiducial 20 and the base 140a,b,c. The connection aid may be located near the bottom portion of the fiducial 20, within the fault interface 120, both, or otherwise, and can include magnetic attraction, adhesives, hook and pile connectors, or any other materials or forces which result in a bond between the fiducial 20 and base 140a,b,c which features a smaller failure strength than relevant portions of either the fiducial or base. Accordingly, when sufficient force is placed on the fiducial 20, the connection aid allows the base to be displaced or dislodged in a manner that allows ready replacement into correct position and orientation.

In use, attachment devices 20, 320, or 420 bearing fiducials and/or active devices are connected to relevant body parts or part of tools, trials, implant components, tables, or other tangible things in the operating room. The fiducials and/or active devices are then registered into the computer aided surgery system in accordance with techniques discussed at length in the documents cited and incorporated by reference above. During surgery, the fiducials and/or active devices allow images of the thing to which they are attached to be represented in accurate position and orientation on a monitor with the aid of computer processing. However, when a fiducial or active device is inadvertently struck with an elbow or implement in a manner that would otherwise deform it in position or orientation or both, or dislodge it the thing to which was attached, instead the fault interface fails and allows the fiducial or active device or reference frame to be dislodged in a manner that permits its ready replacement in a manner that eliminates the necessity to reregister the indicium or the reference frame into the system. For example, the fiducial 20 may be replaced in its correct position, location and orientation with respect to the thing to which it was attached.

Figure 12:
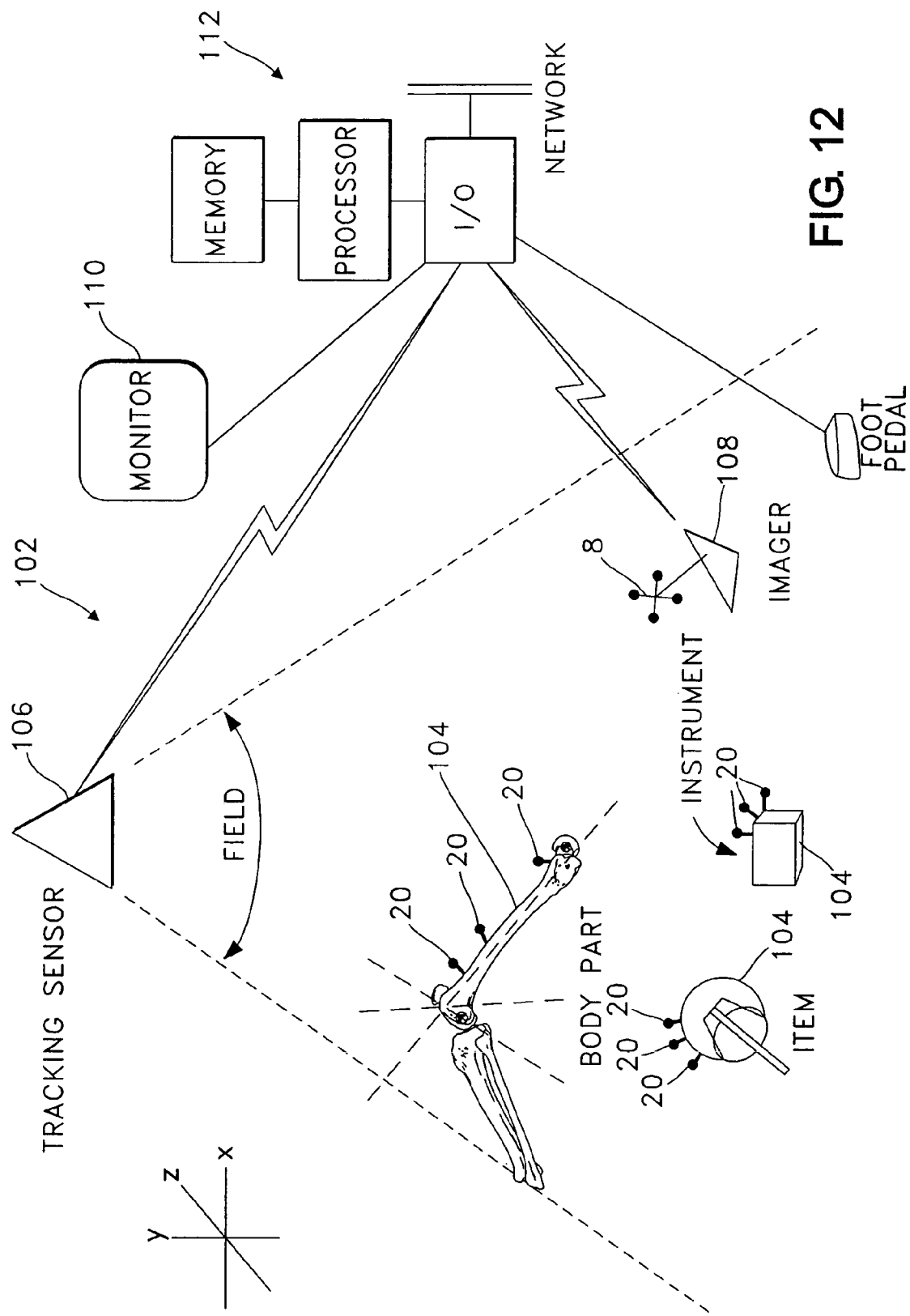
FIG. 12 shows a schematic view of a tracking system according to another embodiment of the present invention.

FIG. 12 shows a tracking system 102 that may utilize modular indicium 20 to track the orientation and/or position of desired items 104 within the tracking sensor's 106 field of vision. Modular indicium 20 or other reference structures 8 may be placed on items 104 to be tracked such that a tracking system 102 can track the position and/or orientation of any desired item in the field of view of the tracking sensor 106. The tracking sensor 106 may relay the position and/or orientation data to a processing functionality 112 which can correlate the data with data obtained from an imaging device 108 and output that data to a suitable output device 110.

Figure 13:
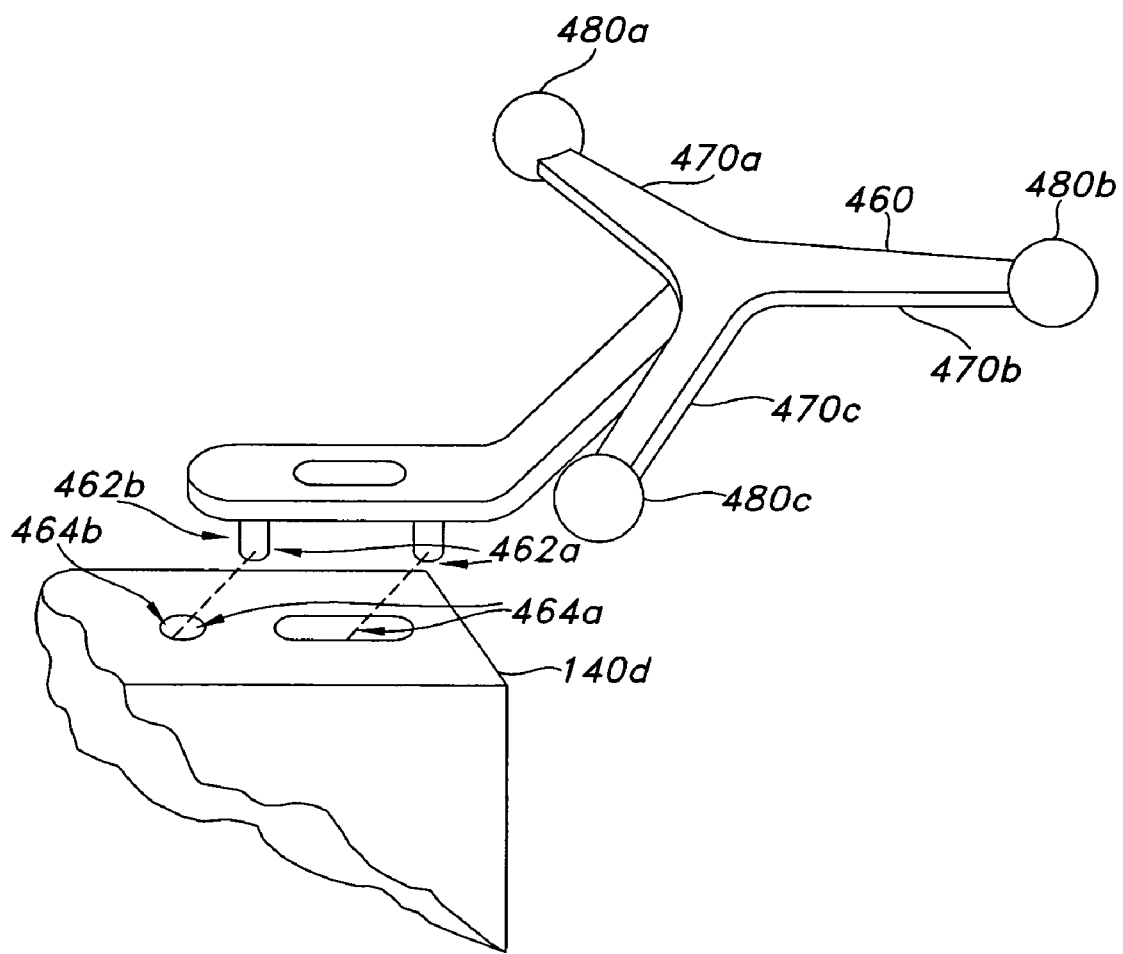
FIG. 13 shows a perspective view of an attachment device of unitary construction, according to one embodiment of the present invention.

FIG. 13 shows yet another embodiment of the present invention in which the attachment device 460 may be of unitary construction. Among other materials and methods of manufacture, this embodiment of the attachment device may be comprised of plastic and may be manufactured by the injection of plastic into a suitable mold. In a particular embodiment, the attachment device contains a set of two protrusions 462a, 462b which correspond to a hole 464b and a slot 464a on an array base 140d. The attachment device 460 in this particular structure is designed to accept additional elements 480a, 480b, and 480c for placement on the extensions 470a, 470b, and 470c on the attachment device 460. These additional elements may comprises active or passive position indicating devices. As with other devices, an additional connection aid may be utilized in this embodiment.

Certain embodiments of the present invention may be comprised of plastic or another material which results in production costs which are relatively low compared to other manufacturing materials. Because of this, the attachment devices and bases may be disposed of after each use. Disposal of used devices and bases eliminates the time and expense necessary for sterilization between uses. It is not necessary that the present invention be comprised of plastic; any device or position indicator which can be manufactured for less expense than it costs to sterilize a used device is contemplated.

The active or passive position indicating devices may be often more expensive, however. To account for such, according to certain embodiments of the present invention, the position indicating devices are manufactured separately from the attachment device. After use, they may be disposed of or easily removed and stored for re-use while the attachment device itself may be disposed.

Figure 14:
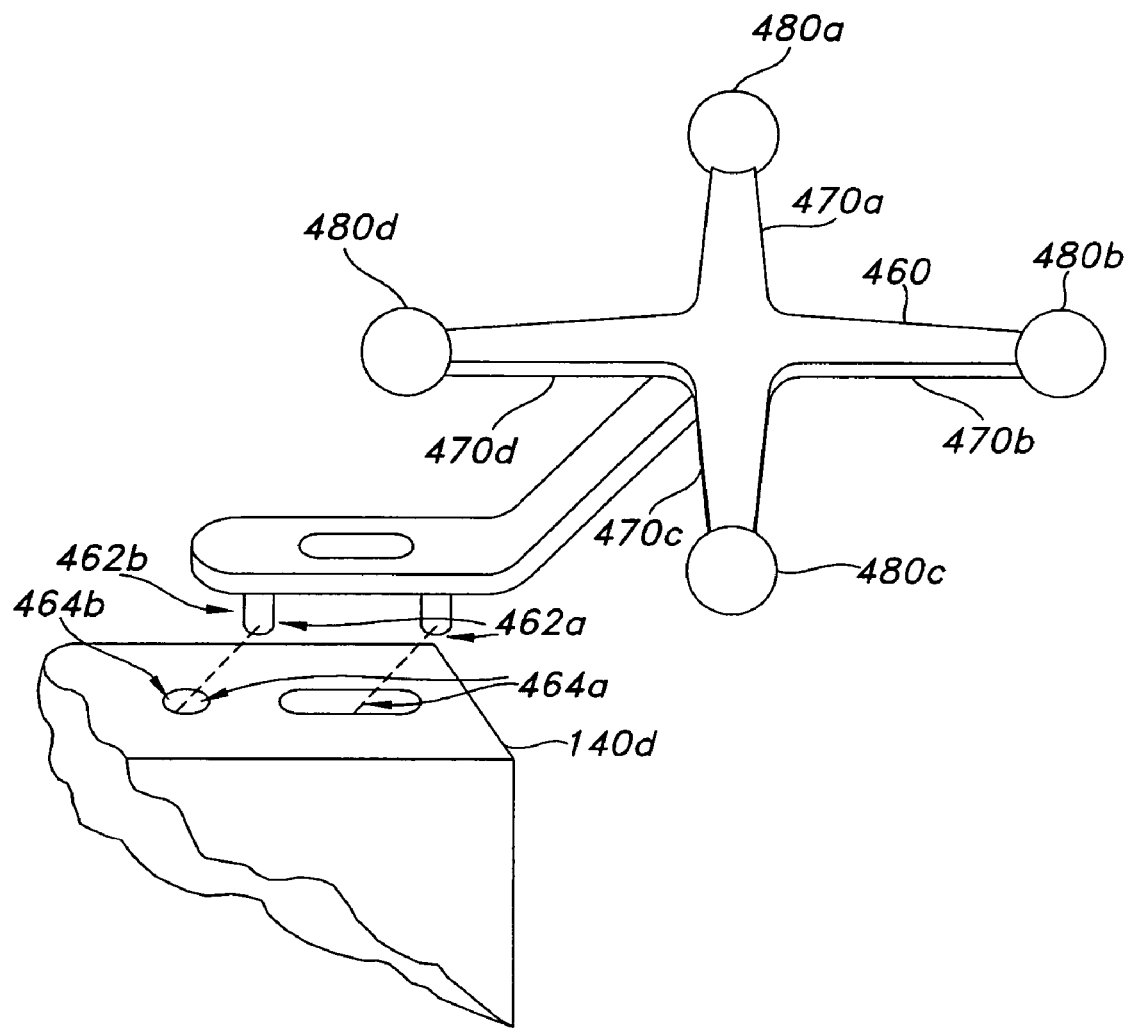
FIG. 14 shows a perspective view of an attachment device with four fiducials according to a certain aspect of the present invention.

FIG. 14 shows a variation of the embodiment of FIG. 13 in which four extensions 480a, 480b, 480c, and 480d, are present on the attachment device. This provides for the use of a further position indicating device that may be registered into the coordinate system.

The foregoing is provided for purposes of disclosure of various aspects and embodiments of the present invention. Changes, deletions, additions or and substitutions may be made to components, combinations, processes, and embodiments disclosed in this document without departing from the scope or spirit of the invention.

What is claimed is:

1. A computer aided surgery navigation system comprising:
   a. a sensor adapted to sense position of a plurality of indicia on a reference frame attached to an item used in surgery;
   b. a computing device adapted to receive information from the sensor about position of the indicia and generate information corresponding to position and location of the item to which the indicia are attached;
   c. a display device adapted to render an image of the item correctly positioned and oriented in correspondence with the position of its indicia as sensed by the sensor; wherein
   d. the reference frame includes an indicia attachment portion configured to hold the plurality of indicia in an asymmetrical array, a base portion comprising an attachment device configured to secure the base portion to the item used in surgery and a connection portion between the indicia attachment portion and the base portion, the connection portion configured to position the plurality of indicia relative to the base portion at a predetermined position and orientation;
   e. the connection portion of the reference frame including a fault interface structure with a mating portion having a male mating part and a female mating part, the male and female mating parts causing the indicia attachment portion to attach to the base portion in the predetermined orientation and position, and wherein an additional connection force other than the frictional force between the male and female mating parts is used to hold the indicia attachment portion to the base portion with a strength lower than a strength of other portions of the reference frame, whereby the fault interface permits disconnection of the indicia attachment portion from the base upon application of any inadvertent force to the reference frame regardless of the direction and moment of the inadvertent force; and
   f. wherein the fault interface structure permits reconnection of the plurality of indicia to the base in the predetermined position and orientation.

2. A system according to claim 1 in which at least one of the indicia or reference frame is comprised of plastic.

3. A system according to claim 1 in which the indicia attachment portion is of unitary construction.

4. A system according to claim 1, wherein the indicia are active devices.

5. A system according to claim 4 in which at least some of the active devices are transponders which emit energy when interrogated.

6. A system according to claim 1 in which the fault interface includes structure adapted to create a friction fit.

7. A system according to claim 1 wherein the attachment device comprises a plurality of pins for attaching the item to a bone.

8. A system according to claim 1 in which the item is a bone screw.

9. A system according to claim 1 in which the item is an implant.

10. A system according to claim 1 in which the additional connection force is magnetic attraction.

11. A system according to claim 1, in which the additional connection force is adhesive.

12. A system according to claim 1, in which the additional connection force is hook and pile connectors.

13. A device for use in a computer aided surgical navigation system, the system comprising a sensor adapted to sense position of a plurality of indicia on a reference frame attached to an item used in surgery; a computing device adapted to receive information from the sensor about position of the indicia and generate information corresponding to position and location of the item to which the indicia are attached; and a display device adapted to render an image of the item correctly positioned and oriented in correspondence with the position of its indicia as sensed by the sensor; the device comprising at least one reference frame, the reference frame including an indicia attachment portion configured to hold the plurality of indicia in an asymmetrical array, a base portion comprising an attachment device configured to secure the base portion to the item used in surgery and a connection portion between the indicia attachment portion and the base portion, the connection portion configured to position the plurality of indicia relative to the base portion at a predetermined position and orientation; wherein the connection portion of the reference frame includes a fault interface structure with a mating portion having a male mating part and a female mating part, the male and female mating parts causing the indicia attachment portion to attach to the base portion in the predetermined orientation and position, and wherein an additional connection force other than the frictional force between the male and female mating parts is used to hold the indicia attachment portion to the base portion with a strength lower than of other portions of the reference frame, whereby the fault interface permits disconnection of the indicia attachment portion from the base upon application of any inadvertent force to the reference frame regardless of the direction and moment of the inadvertent force; and wherein the fault interface structure permits reconnection of the plurality of indicia to the base in the predetermined position and orientation.

14. A device according to claim 13 in which at least one of the indicia or the reference frame is comprised of plastic.

15. A device according to claim 13 in which the indicia attachment portion is of unitary construction.

16. A process for conducting computer aided surgery, comprising:
   I. providing a computer aided surgery system, wherein providing the computer aided surgery system comprises:
      a. providing a sensor adapted to sense position of a plurality of indicia on a reference frame attached to an item used in surgery;
      b. providing a computing device adapted to receive information from the sensor about position of the indicia and generate information corresponding to position and location of the item to which the indicia are attached;
      c. providing a display device adapted to render an image of the item correctly positioned and oriented in correspondence with the position of its indicia as sensed by the sensor;
      d. providing a device comprising at least one reference frame, the reference frame including an indicia attachment portion configured to hold the plurality of indicia in an asymmetrical array, a base portion comprising an attachment device configured to secure the base portion to the item used in surgery and a connection portion between the indicia attachment portion and the base portion, the connection portion configured to position the plurality of indicia relative to the base portion at a predetermined position and orientation; wherein e. the connection portion of the reference frame includes a fault interface structure with a mating portion having a male mating part and a female mating part, the male and female mating parts causing the indicia attachment portion to attach to the base portion in the predetermined orientation and position, and wherein an additional connection force other than the frictional force between the male and female mating parts is used to hold the indicia attachment portion to the base portion with a strength lower than a strength of other portions of the reference frame, whereby the fault interface permits disconnection of the indicia attachment portion from the base upon application of any inadvertent force to the reference frame regardless of the direction and moment of the inadvertent force; and f. wherein the fault interface structure permits reconnection of the plurality of indicia to the base in the predetermined position and orientation:

II. registering the indicia into the system;

III. navigating the item during surgery using the image rendered by the rendering functionality;

IV. applying a force to the reference frame whereby the indicia attachment portion is disconnected from the base portion; and V. repositioning the indicium into correct position and orientation relative to the item by reconnecting the indicia attachment portion to the base portion with the fault interface structure; and VI. continuing to navigate the item during surgery without the need to reregister the indicium into the system.

17. A system according to claim 1, in which at least some of the indicia comprise reflective surfaces adapted to be sensed by an infrared sensor device.

* * * * *